United States Patent
Vivancos Martinez et al.

(10) Patent No.: US 11,007,152 B2
(45) Date of Patent: May 18, 2021

(54) PHARMACEUTICAL COMPOSITION COMPRISING AMORPHOUS LENALIDOMIDE AND AN ANTIOXIDANT

(71) Applicant: Synthon B.V., Nijmegen (NL)

(72) Inventors: Marta Vivancos Martinez, Sant Boi de Llobregat (ES); Lisardo Alvarez Fernandez, Sant Boi de Llobregat (ES); Jose Velada Calzada, Nijmegen (NL)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 16/388,195

(22) Filed: Apr. 18, 2019

(65) Prior Publication Data
US 2019/0240157 A1 Aug. 8, 2019

Related U.S. Application Data

(60) Division of application No. 15/978,854, filed on May 14, 2018, now Pat. No. 10,328,028, which is a continuation of application No. PCT/EP2016/082318, filed on Dec. 22, 2016.

(30) Foreign Application Priority Data

Dec. 22, 2015 (EP) ..................... 15202069

(51) Int. Cl.
*A61K 9/16* (2006.01)
*A61K 31/454* (2006.01)
*A61P 35/00* (2006.01)

(52) U.S. Cl.
CPC .......... *A61K 9/1635* (2013.01); *A61K 9/1617* (2013.01); *A61K 31/454* (2013.01)

(58) Field of Classification Search
CPC ... A61K 31/454; A61K 9/1635; A61K 9/1617
See application file for complete search history.

(56) References Cited

U.S. PATENT DOCUMENTS

2012/0046315 A1  2/2012  Rimkus et al.

FOREIGN PATENT DOCUMENTS

| CN | 103705485 | * | 4/2014 | ........... A61K 31/454 |
|---|---|---|---|---|
| EP | 925294 | | 12/2002 | |
| WO | WO2005/023192 | | 3/2005 | |
| WO | WO2009/114601 | | 9/2009 | |
| WO | WO2010/061209 | | 11/2009 | |
| WO | WO2010/100476 A2 | | 3/2010 | |
| WO | WO2010/054833 | | 5/2010 | |
| WO | WO2011/111053 | | 9/2011 | |
| WO | WO2013/165973 A1 | | 11/2013 | |
| WO | WO2014/160686 A1 | | 3/2014 | |

OTHER PUBLICATIONS

Lai, et al. "Pharmaceutical composition used for treating myelodysplastic syndrome, comprises lenalidomide, carrier, solubilizer, disintegrant, lubricant, glidant, and binder" Section Ch, Week 201435 Thomson Scientific, AN 2014-K57600, XP002767155 Abstraction of CN 103705485 A1, Apr. 9, 2014.

Gomathi, et al., "Studies on drug-polymer interaction, in vitro release and cytotoxicity from chitosan particles excipient" International Journal of Pharmaceutics, vol. 468, No. 1, Apr. 15, 2014, pp. 214-222.

Gong et al., "Pharmaceutical composition prepared by dissolving water-insoluble medicine and solid dispersing carrier in organic solvent, uniformly spraying on blank pill core, and drying" Section Ch, Week 200969 Thomson Scientific, AN 2009-P17646 XP002767156 Abstraction of CN 101537184A, Sep. 23, 2009.

\* cited by examiner

*Primary Examiner* — Irina Neagu
(74) *Attorney, Agent, or Firm* — Buscher Patent PLLC

(57) ABSTRACT

The present invention relates to a pharmaceutical composition comprising amorphous lenalidomide, or a pharmaceutically acceptable salt thereof, with a synthetic antioxidant and one or more pharmaceutically acceptable excipients. The invention further relates to the process to manufacture such a compositions and the use of said composition as a medicament, particularly in the treatment of in the treatment of multiple myeloma and myelodyplastic syndromes.

3 Claims, No Drawings

PHARMACEUTICAL COMPOSITION COMPRISING AMORPHOUS LENALIDOMIDE AND AN ANTIOXIDANT

CROSS-REFERENCE TO RELATED APPLICATIONS

The present application is a Divisional under 35 U.S.C. §§ 120 and 121 of U.S. application Ser. No. 15/978,854, filed May 14, 2018, which is a bypass Continuation of PCT/EP2016/082318 filed on Dec. 22, 2016, which claims priority of EP15202069.9 filed Dec. 22, 2015, the entire contents of which are hereby incorporated by reference.

BACKGROUND OF THE INVENTION

Lenalidomide, chemically (RS)-3-(4-Amino-1-oxo 1,3-dihydro-2H-isoindol-2-yl)piperidine-2,6-dione of formula (I),

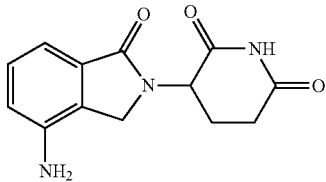 [SMILES: Nc1cccc2c1CN(C1CCC(=O)NC1=O)C2=O]

is a pharmaceutically active compound used for the treatment of multiple myeloma and Myelodysplastic syndromes.

The compound was discovered by Celgene and is disclosed in EP925294. Lenalidomide is the active ingredient in the medicinal product sold under the brand name Revlimid®.

Lenalidomide exhibits polymorphism. WO2005023192 discloses crystalline forms of lenalidomide, its process of preparation, compositions comprising these crystalline forms and its use for treatment of diseases. Polymorph B is the most stable form and is present in the marketed tablets. Compositions comprising both amorphous and crystalline lenalidomide are also disclosed in this application. Other polymorphic forms of lenalidomide are disclosed in WO2011111053. The prior art thus teaches that lenalidomide crystallizes very easily. Moreover, it was experienced in our laboratory that polymorphic transitions of lenalidomide take place rather easily, especially in drug product.

Lenalidomide is slightly soluble in water. Conventional approaches to increase solubility consist on micronizing the API. Nevertheless, it was experienced in our laboratory that micronization of lenalidomide gave partially amorphous solid, which readily converts to other crystalline forms. It is known that generally the solubility of amorphous forms is higher compared to the solubility of crystalline forms. In view of this, it would be desirable to produce stable amorphous lenalidomide and to find a robust process for making such a stable amorphous lenalidomide.

WO2010054833 and WO2009114601 disclose solid dispersions containing amorphous lenalidomide.

It has been found that amorphous lenalidomide generates more impurities, especially oxidative impurities, if compared with the crystalline lenalidomide, making the use of amorphous lenalidomide in a commercial scale very difficult.

Revlimid® is in the market as a crystalline form, the market formulation, which has been submitted to extended stability studies does not contain an antioxidant.

WO2010061209 relates to new crystalline forms of lenalidomide in the description it is mentioned that preservatives and chelatings agents may be added to improve storage stability. This application however does not suggest that the replacement of crystalline lenalidomide for amorphous lenalidomide will result in additional stability problems.

Thus in view of the stability problems of amorphous lenalidomide, there is a need for pharmaceutical compositions comprising amorphous lenalidomide, or a pharmaceutically acceptable salt thereof, which are stable and suitable for use on a commercial scale.

BRIEF DESCRIPTION OF THE INVENTION

The present invention relates to a pharmaceutical composition comprising amorphous lenalidomide, or a pharmaceutically acceptable salt thereof, with a synthetic antioxidant and one or more pharmaceutically acceptable excipients.

It also provides a process for preparing said amorphous lenalidomide comprising the steps:
  a) Dissolving lenalidomide or a pharmaceutically acceptable salt thereof with a polymer and a synthetic antioxidant;
  b) Spray or spray drying the solution of step a) on a carrier to obtain a granule;
  c) Blending the granule with further excipients;
  d) Optionally encapsulating the blend of step c.

An alternative process to manufacture the amorphous lenalidomide compositions of the present invention comprises the steps:
  a) Dissolving lenalidomide or a pharmaceutically acceptable salt thereof with a polymer;
  b) Spray or spray drying the solution of step a) on a carrier to obtain a granule;
  c) Blending the granule with a synthetic antioxidant and further excipients;
  d) Optionally encapsulating the blend of step c.

Said pharmaceutical composition may be used as a medicament, particularly in the treatment of multiple myeloma and myelodyplastic syndromes.

DETAILED DESCRIPTION OF THE INVENTION

The present invention relates to a pharmaceutical composition comprising amorphous lenalidomide, or a pharmaceutically acceptable salt thereof, with a synthetic antioxidant and one or more pharmaceutically acceptable excipients.

Drugs that can exist in either amorphous or crystalline form tend to crystallize over time when present in amorphous state because the crystalline form of the drug is a lower-energy state than the amorphous form.

WO2010/061209 suggests that preservatives and chelatings agents may be added to their crystalline polymorph lenalidomide compositions to improve storage stability.

Crystalline lenalidomide is in the European market since 2007 as Revlimid®. This commercial formulation does not contain antioxidants. In order to get approved by EMA (European medicines agency), a drug has to comply with the guidelines and has to be submitted to a thorough stability testing program, including stress testing. The scientific assessment of Revlimid by the EMA (26Jun. 2007) stated that all results remained within the specification. Therefore, it can be concluded that the crystalline marketed lenalidomide does not present oxidation problems.

It was surprisingly found that the replacement of crystalline lenalidomide for amorphous lenalidomide has a negative influence on the chemical stability of the compound. In particular oxidative degradation of the amorphous lenalidomide has been observed. This occurs even when a high protective packaging as Al/Al is used. The increase of these oxidatives impurities is inherent to the amorphous form and it is not seen with other forms as Form A or B (these polymorphs are described on WO2005023192).

Degradation of the amorphous lenalidomide affects the stability of the pharmaceutical preparation, making it difficult to be used in a commercial scale. The observed oxidative degradation of amorphous lenalidomide was unexpected as the dry crystalline form is known to be very stable.

Accordingly it would be desirable to provide a pharmaceutical amorphous lenalidomide which has a higher solubility than the crystalline lenalidomide composition but is less prone to oxidative degradation.

As used herein, the term oxidative degradation refers to a chemical reaction of lenalidomide with oxygen during manufacture and/or storage producing oxidative impurities.

A method for avoiding the oxidative impurities is to use a high protective packaging material such as Al/Al. However, the inventors found that this package was not preventing the formation of oxidative degradation.

Another method to prevent oxidative degradation is the use of antioxidants.

Antioxidants are substances added in small quantities to hydrocarbons which are susceptible to oxidation. Antioxidants work in different ways. Antioxidants can be natural for instance ascorbic acid, vitamin E, tartaric acid or citric acid or synthetic. The synthetic antioxidants can be classified in primary and secondary antioxidants. In primary antioxidants (also called free-radical scavengers), antioxidative activity is implemented by the donation of an electron or hydrogen atom to a radical derivative. These antioxidants are usually hindered amines (p-Phenylene diamine, trimethyl dihydroquinolines, alkylated diphenyl amines) or substituted phenolic compounds with one or more bulky functional groups such as a tertiary butyl at 2,6 position commonly. Butylated hydroxytoluene (BHT) is a common example of hindered phenolic antioxidant. Primary antioxidants are free radical scavengers which combine with peroxy radicals and break autocatalytic cycle. In secondary antioxidants (also called peroxide decomposers), activity is implemented by the removal of an oxidative catalyst and the consequent prevention of the initiation of oxidation. Examples of peroxide decomposer type of antioxidant are trivalent phosphorous and divalent sulfur-containing compounds such as sulfides, thiodipropionates and organophosphites.

Antioxidant effectiveness is related to activation energy, rate constants, oxidation-reduction potential, ease with which the antioxidant is lost or destroyed (volatility and heat susceptibility), and antioxidant solubility.

It has been surprisingly found by the present inventors that only synthetic antioxidants stabilize the amorphous lenalidomide. Therefore, suitable antioxidants for use according to the invention are the synthetic antioxidants. Preferred antioxidants are primary synthetic antioxidants, more preferred are phenolic substituted compounds and even more preferred are monophenolic antioxidants, the most preferred antioxidants are BHT or BHA. BHT and BHA interrupt the free radical chain reaction donating H. to the free radicals formed during oxidation becoming a radical themselves. These radical intermediates are stabilized by the resonance delocalization of the electron within the aromatic ring and formation of quinone structures.

In the pharmaceutical composition of the invention the synthetic antioxidant is present in an amount of 0.001 to 5% by total weight, preferably from 0.03 to 3% by total weight, even more preferably from 0.05 to 0.85 by total weight even more preferred 0.05 to 0.5 by total weight even more preferred from 0.04 to 0.1% by total weight.

There are different ways of obtaining amorphous lenalidomide. Among them by forming inclusion complexes such as cyclodextrines, adsorbates such as syloid or by solid dispersions. In a preferred embodiment of the invention the amorphous lenalidomide is stabilised in a polymer solid dispersion.

The stabilizing of amorphous lenalidomide has been attributed to an antiplasticization effect since solid dispersions typically possess higher glass transition temperatures than the pure amorphous drug, thus resulting in a lower molecular mobility that prevents phase transition. The stability may also be due to formation of specific drug-polymer interactions such as hydrogen bonds. Polymers that are commonly used to stabilize the amorphous state in a solid dispersion include but are not limited to HPMC, HPMCAS, HPMCP, CAP, Eudragit and N-vinylpyrrolidones. Preferred polymers to use in the present invention are pyrrolidones such as PVP or coPVP.

In a preferred embodiment, the compositions include lenalidomide and the polymer present in weight ratios ranging from 1:1 to 1:6, from 1:2 to 1:5, most preferred from 1:4 to 1:5. Higher ratios give dissolution problems.

At least a major portion of lenalidomide, or a pharmaceutically acceptable salt thereof, in the composition is amorphous. The term "a major portion" of lenalidomide, or a pharmaceutically acceptable salt thereof, means that at least 60% of the drug is in amorphous form, rather than a crystalline form. Preferably, lenalidomide, or a pharmaceutically acceptable salt thereof, in the solid dispersion is at least 80% in amorphous form. More preferably, lenalidomide, or a pharmaceutically acceptable salt thereof, in the composition is "almost completely amorphous" meaning that the amount of lenalidomide, or a pharmaceutically acceptable salt thereof, in the amorphous form is at least 90% as measured by powder X-ray diffraction or any other standard quantitative measurement. Most preferably, lenalidomide, or a pharmaceutically acceptable salt thereof, in the composition is in a completely amorphous form within the detection limits of the techniques used for characterization.

The excipients to be used in accordance with the present invention are well-known and are those excipients which are conventionally used by the person skilled in the art. Depending on the dosage form chosen for the pharmaceutical composition, the person skilled in the art will be able to select suitable pharmaceutically acceptable excipients. Preferably, the dosage form is an immediate release capsule and the pharmaceutically acceptable excipients are chosen from one or more binders, diluents, disintegrants, glidants, lubricants, stabilizers, surface active agents or pH-adjusting agents. More preferably, the composition of the present invention comprises a diluent, a disintegrant and a lubricant.

The diluent to be used in accordance with the present invention may be any diluent known to a person of ordinary skill in the art. Particularly, the diluent to be used in accordance with the present invention is an inorganic diluent, polysaccharide, mono- or disaccharide or sugar alcohol. Microcrystalline cellulose or anhydrous dicalcium phosphate is a particularly preferred diluent.

The disintegrant to be used in accordance with the present invention may be any disintegrant known to a person of ordinary skill in the art. Suitable disintegrants to be used in accordance with the present invention are selected from the group consisting of microcrystalline cellulose, croscarmellose sodium, crospovidone or sodium starch glycolate. Croscarmellose sodium and starch are particularly preferred disintegrant.

The lubricant to be used in accordance with the present invention may be any lubricant known to a person of ordinary skill in the art. Magnesium stearate is a particularly preferred lubricant.

During preparation and storage of the pharmaceutical compositions of the present invention, lenalidomide, or a pharmaceutically acceptable salt thereof, remains in the amorphous form.

The present invention still further provides a process to prepare pharmaceutical compositions comprising amorphous lenalidomide, a synthetic antioxidant, a polymer and one or more pharmaceutically acceptable excipients.

Lenalidomide and the polymer may be dissolved in the same solvent or in different solvents and then combined.

In an advantageous variant of the process of the present invention, lenalidomide or a pharmaceutically acceptable salt thereof is dissolved in acidic water or a mixture of acidic water and a polar organic solvent and, the polymer is added to this solution. Preferred ratio organic solvent:acidic water is from 8:2 to 1:9, more preferred is 7:3 w/w. Preferred polar organic solvents are alcohols, particularly ethanol or methanol, ethers, particularly tetrahydrofuran, ketones, particularly acetone and acetonitrile. Preferably, 0.1N aqueous HCl or a mixture of acetone and 0.1N aqueous HCl is used. Preferred ratio of acetone:0.1N aqueous HCl is 7:3 w/w. This ratio gives an optimal impurity profile.

The methods and equipment to carry out the process to form formulation of the present invention are well known in the art.

In one possible embodiment the lenalidomide, or a pharmaceutically acceptable salt thereof, and a polymer are dissolved in a suitable solvent or solvent mixture, then the solvent is evaporated and the obtained mixture is blended with a synthetic antioxidant and further excipients.

Another possible method is adding the synthetic antioxidant as intragranular excipient. The addition of the synthetic antioxidant intragranularly is preferred because the antioxidant is better distributed.

In a yet preferred embodiment, lenalidomide, or a pharmaceutically acceptable salt thereof, is dissolved in a suitable solvent or solvent mixture, the polymer and the synthetic antioxidant are added and then the solvent is evaporated to obtain a granule. The granule is densified by means of dry granulation, milled and blended with further excipients.

The addition of the antioxidant in the solution has the advantage of decreasing the oxidizing compounds in the formula that could come from the polymer (such as peroxides), preventing in this way the increase of oxidative degradation impurities during stability.

The mixtures obtained after blending can be further encapsulated.

Examples of equipments to carry out this evaporation method are fluid bed, high shear mixed and spray drying. When the fluid bed technology is used additionally a pharmaceutical carrier is needed. Lactose, cellulose, starch and phosphates are the preferred pharmaceutical carriers. Pregelatinized starch, MCC and calcium phosphate are the most preferred pharmaceutical carriers. If MCC is used an extra step to density the final granules is required. With MCC as carrier a more stable formulation is obtained.

The compositions of the present invention can also be prepared by hot melting lenalidomide, or a pharmaceutically acceptable salt thereof, with the synthetic antioxidant and optionally adding a polymer. This process can be carried out without the use of solvents.

The process comprises mixing or granulating the lenalidomide with one or more pharmaceutically acceptable excipients, followed by encapsulation, using equipment and methods well-known to the skilled artisan. In an advantageous variant of the process of the present invention, a solution of lenalidomide, or a pharmaceutically acceptable salt thereof, the synthetic antioxidant, and the polymer was sprayed over the pharmaceutical carrier e.g. the diluent, in a fluidized bed and the resulting granulate/blend was compacted and milled by dry granulation and finally mixed with one or more pharmaceutically acceptable extragranular excipients, followed by encapsulation. Preferably, a solution of lenalidomide, BHT and co-PVP, in acidic water/acetone was sprayed over microcrystalline cellulose (MCC) in a fluidized bed, after which the granulate/powder blend was compacted and milled by dry granulation and finally mixed with MCC, croscarmellose sodium and magnesium stearate, followed by encapsulation. Preferably, HPMC or gelatine capsules are used.

In another advantageous variant of the process of the present invention, a solution of lenalidomide, or a pharmaceutically acceptable salt thereof, and a polymer was sprayed over the pharmaceutical carrier e.g. the diluent, in a fluidized bed and the resulting granulate/blend was mixed with a synthetic antioxidant and one or more pharmaceutically acceptable extragranular excipients, followed by encapsulation. Preferably, a solution of lenalidomide and PVP in acidic water/acetone was sprayed over MCC in a fluidized bed, after which the granulate/powder blend was mixed with BHT, microcrystalline cellulose or starch, croscarmellose sodium and magnesium stearate, followed by encapsulation. Preferably, HPMC or gelatine capsules are used.

In a preferred embodiment, lenalidomide form A crystal with an XRPD pattern having peaks at approximately 8, 14.5, 16, 17.5, 20.5, 24, and 26 degrees 2θ is used as starting material for carrying out the above processes.

The pharmaceutical compositions prepared according to the present invention display dissolution behaviour typical for immediate-release formulations. The compositions of the present invention exhibit a dissolution rate of at least 85% in 15 minutes when tested in 900 ml SGF pH 1.2, pH 2, acetate buffer pH 4.5 or phosphate buffer pH 6.8 in a USP apparatus I at 100 rpm in standard vessels.

The pharmaceutical compositions of the present invention are packaged in blister pack material. The blister pack materials to be used in accordance with the present invention may be any blister pack material known to a person of ordinary skill in the art. Suitable blister pack materials to be used in accordance with the present invention are selected from the group of Aclar, PVC/Alu, Duplex/Alu, Triplex/Alu and Alu/Alu. To ensure protection of the compositions of the present invention from e.g. moisture and thereby preventing polymorphic conversions, Alcar, Triplex/Alu and Alu/Alu are particularly preferred blister pack materials.

After storage of the pharmaceutical compositions in these blister pack materials for 1 month at 40° C./75% RH, XRPD analysis showed no reflections in accordance with crystalline lenalidomide.

The pharmaceutical composition in accordance with the present invention may be used as a medicament. The pharmaceutical composition typically may be used in the treatment of multiple myeloma and myelodyplastic syndromes.

The following examples are intended to illustrate the scope of the present invention but not to limit it thereto.
In order to detect the impurities a HPLC with an Analytical column, XSelect HSS T3 (Waters, 150×4.6 mm, dp=2.5 µm) was used. Mobile phase A: phosphate buffer pH 3.5. Mobile phase B: Acetonitrile (ACN).

EXAMPLES

Example 1, Lenalidomide:PVP (Weight Ratio 1:4)

The stabilized complex of lenalidomide with povidone has a ratio of API:PVP=1:4 w/w.
(1) Dissolution: 298.25 grams of povidone are added and dissolved in 1704 mL of acetone:0.1N HCl (7:3 w/w) solution under heating (50° C.) and stirring conditions. Once the povidone is completely dissolved, 74.56 grams of lenalidomide are incorporated into the dissolution.
(2) Spraying: the (1) resulting dissolution is sprayed into a fluid bed equipment over the filler (972.74 g of anhydrous dicalcium phosphate) and subsequently dried, obtaining granules.
(3) Total mixture: the amounts of the following excipients are adjusted base on the granulation yield obtained in the previous step: 277.95 g of microcrystalline cellulose, 51.0 g of sodium croscarmellose are mixed with the (2) resulting granules. 17 g of magnesium stearate are sieved through a 0.5 mm mesh and mixed with the previous blend.
(4) This final blend is used to study the influence of the different antioxidants: no addition, BHT (0.1-0.5%), citric acid (0.3%-2%), tartaric acid (2-3%) in the following way:
    (4.1) No antioxidant: Final blend get in step (4);
    (4.2) 0.1% BHT: 0.01 g of BHT are milled and mixed for 5 min with 9.99 g of final blend (4);
    (4.3) 0.5% BHT: 0.05 g of BHT are milled and mixed for 5 min with 9.95 g of final blend (4);
    (4.4) 0.3% citric ac: 0.03 g of citric ac are milled and mixed for 5 min with 9.97 g of final blend (4);
    (4.5) 2% citric ac: 0.2 g of citric ac are milled and mixed for 5 min with 9.8 g of final blend (4);
    (4.6) 2% tartaric ac: 0.2 g of tartaric ac are milled and mixed for 5 min with 9.8 g of final blend (4);
    (4.7) 3% tartaric ac: 0.3 g of tartaric ac are milled and mixed for 5 min with 9.7 g of final blend (4).
(5) Different blends are packaged in HDPE bottles (open dish) and stored 1 week at 55° C./90% RH. Impurities are tested after this period of time.
Results

|  | No antioxidant | BHT 0.1% | BHT 0.5% | Citric acid 0.3% | Citric acid 2.0% | Tartaric acid 2.0% | Tartaric acid 3.0% |
|---|---|---|---|---|---|---|---|
| Initial | | | 1 week 55° C./90% RH, Open dish | | | | |
| | Total 0.37% | Total 1.01% | Total 0.67% | Total 0.66% | Total 0.97% | Total 0.96% | Total 0.93% Total 1.12% |

Example 2, Lenalidomide:Povidone (Weight Ratio 1:5) without Antioxidant, Different Packaging (1) The stabilized complex of lenalidomide with povidone has a ratio of API:PVP=1:5 w/w.
(2) Dissolution: 152.93 grams of povidone are added and dissolved in 714.6 mL of acetone:0.1N HCl (7:3 w/w) solution under heating (50° C.) and stirring conditions. Once the povidone is completely dissolved, 30.59 grams of lenalidomide are incorporated into the dissolution.
(3) Spraying: the (2) resulting dissolution is sprayed into a fluid bed equipment over the filler (368.46 g of microcrystalline cellulose) and subsequently dried, obtaining granules.
(4) Total mixture: the amounts of the following excipients are adjusted base on the granulation yield obtained in the previous step: 17.25 g of sodium croscarmellose are mixed with the (2) resulting granules. 5.75 g of magnesium stearate are sieved through a 0.5 mm mesh and mixed with the previous blend.
(5) Capsules: the (4) final blend is then encapsulated into size 0 capsules.
Composition

| Lenalidomide | 25 mg |
|---|---|
| Povidone K-12 | 125 mg |
| Microcrystalline cellulose | 301.18 mg |
| Sodium Croscarmellose | 14.10 mg |
| Magnesium stearate | 4.7 mg |
| Gelatine capsules size | 0 |

Impurities are measured after 1 month in accelerated conditions (40° C./75% RH) in two different packaging material: low protective packaging (PVP/PVDC/Al) and high protective packaging (Al/Al).
Results:

| Initial | 1 month (40° C./75% RH) | |
|---|---|---|
| Total 0.72% | Al/Al | PVC/PVDC/Al |
| | Total 0.90% | Total 1.65% |

Example 3, Lenalidomide:Povidone (Weight Ratio 1:5), Addition Antioxidant in Different Packaging (1) The stabilized complex of lenalidomide with povidone has a ratio of API:PVP=1:5 w/w.
(2) Dissolution: 212.77 grams of povidone are added and dissolved in 996.56 mL of acetone:0.1N HCl (7:3 w/w) solution under heating (50° C.) and stirring conditions. Once the povidone is completely dissolved, 42.55 grams of lenalidomide and 0.8 g of BHT are incorporated into the dissolution.

(3) Spraying: the (2) resulting dissolution is sprayed into a fluid bed equipment over the filler (431.84 g of microcrystalline cellulose) and subsequently dried, obtaining granules.

(4) Total mixture: the amounts of the following excipients are adjusted base on the granulation yield obtained in the previous step: 80.0 g of microcrystalline cellulose, 24.0 g of sodium croscarmellose are mixed with the (2) resulting granules. 8.0 g of magnesium stearate are sieved through a 0.5 mm mesh and mixed with the previous blend.

(5) Capsules: the (4) final blend is then encapsulated into size 0 capsules.

Composition

| | |
|---|---|
| Lenalidomide | 25 mg |
| Povidone K-12 | 125 mg |
| Microcrystalline cellulose | 300.71 mg |
| Sodium Croscarmellose | 14.10 mg |
| Butylhydroxytoluene | 0.47 mg |
| Magnesium stearate | 4.7 mg |
| Gelatine capsules size | 0 |

Impurities are measured after 1 month in accelerated conditions (40° C./75% RH) in two different packaging material: low protective packaging (PVP/PVDC/Al) and high protective packaging (Al/Al). Results:

| Initial | 1 month (40° C./75% RH) | |
|---|---|---|
| Total 0.13% | Al/Al | PVC/PVDC/Al |
| | Total 0.10% | Total 0.33% |

Example 4, Lenalidomide:Co-Povidone (Weight Ratio 1:5), Addition Antioxidant Intragranular (1) The stabilized complex of lenalidomide with co-povidone has a ratio of API:PVP=1:5 w/w.

(2) Dissolution: 833.33 grams of co-povidone are added and dissolved in 3813.88 g of acetone:0.1N HCl (7:3 w/w) solution under heating (50° C.) and stirring conditions. Once the co-povidone is completely dissolved, 166.67 grams of lenalidomide and 3 g of BHT are incorporated into the dissolution.

(3) Spraying: the (2) resulting dissolution is sprayed into a fluid bed equipment over the filler (1577 g of microcrystalline cellulose) and subsequently dried, obtaining granules.

(4) The obtained granules are compacted using a roller compactor equipment and subsequently milled through 2 and 0.8 mm screen size.

(5) Total mixture: the amounts of the following excipients are adjusted base on the milled granules yield obtained in the previous step: 300.0 g of microcrystalline cellulose, 90.0 g of sodium croscarmellose are mixed with the (2) resulting granules. 30.0 g of magnesium stearate are sieved through a 0.5 mm mesh and mixed with the previous blend.

(6) Capsules: the (5) final blend is then encapsulated into size 0 capsules.

Composition

| | |
|---|---|
| Lenalidomide | 25 mg |
| Povidone K-12 | 125 mg |
| Microcrystalline cellulose | 281.55 mg |
| Sodium Croscarmellose | 13.5 mg |
| Butylhydroxytoluene | 0.45 mg |
| Magnesium stearate | 4.5 mg |
| Gelatine capsules size | 0 |

The invention claimed is:

1. A lenalidomide pharmaceutical granule, comprising a diluent carrying a polymer composition, wherein said polymer composition comprises a polymer containing a solid dispersion of amorphous lenalidomide, or a pharmaceutically acceptable salt thereof, and a monophenolic antioxidant compound;

wherein said polymer is PVP or co-PVP and the lenalidomide and the polymer are present in a weight ratio ranging from 1:1 to 1:6;

and wherein said antioxidant is BHA or BHT.

2. The granule according to claim 1, wherein said diluent is selected from the group consisting of pregelatinized starch, microcrystalline cellulose (MCC), and calcium phosphate.

3. The granule according to claim 1, wherein said diluent is MCC.

* * * * *